United States Patent
Sumaily

(10) Patent No.: US 10,925,590 B1
(45) Date of Patent: Feb. 23, 2021

(54) UVULA RETRACTOR AND UVULA RETRACTING SYSTEM

(71) Applicant: KING SAUD UNIVERSITY, Riyadh (SA)

(72) Inventor: Ibrahim Ali Sumaily, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/777,782

(22) Filed: Jan. 30, 2020

(51) Int. Cl.
| | |
|---|---|
| A61B 17/02 | (2006.01) |
| A61B 17/24 | (2006.01) |
| A61B 1/07 | (2006.01) |
| A61B 1/267 | (2006.01) |
| A61B 1/32 | (2006.01) |

(52) U.S. Cl.
CPC ............ *A61B 17/0206* (2013.01); *A61B 1/07* (2013.01); *A61B 1/267* (2013.01); *A61B 1/32* (2013.01); *A61B 17/24* (2013.01)

(58) Field of Classification Search
CPC ....... A61B 17/0206; A61B 17/24; A61B 1/07; A61B 1/267; A61B 1/32; A61B 1/06; A61B 1/24
See application file for complete search history.

(56) References Cited

U.S. PATENT DOCUMENTS

| 2,947,305 | A | * | 8/1960 | Storz | ........................ | A61B 1/24 |
| | | | | | | 600/239 |
| 3,616,792 | A | * | 11/1971 | Pleet | ........................ | A61B 1/07 |
| | | | | | | 600/239 |
| 4,052,980 | A | | 10/1977 | Grams et al. | | |
| 6,267,591 | B1 | | 7/2001 | Barstow | | |
| 8,409,088 | B2 | | 4/2013 | Grey et al. | | |
| 2004/0242969 | A1 | * | 12/2004 | Sherts | ................ | A61B 17/0293 |
| | | | | | | 600/231 |
| 2005/0279355 | A1 | | 12/2005 | Loubser | | |

FOREIGN PATENT DOCUMENTS

GB 146475 A 8/1921

OTHER PUBLICATIONS

"Tebbetts Retractor with Fiber-optic Guide and Suction Blade," 2016 Omega Surgical Instruments Ltd. (www.omegahealthcare.co.uk/tebbetts-retractor-with-fibre-optic-guide-and-suction-blade-p-12079).

* cited by examiner

*Primary Examiner* — Kevin T Truong
*Assistant Examiner* — Tracy L Kamikawa
(74) *Attorney, Agent, or Firm* — Nath, Goldberg & Meyer; Richard C. Litman

(57) ABSTRACT

The uvula retractor is an elongate, arcuate body having a hooked handle at one end and a raised platform or flat spoon at the opposite end for lifting the uvula for access to the region behind the uvula. The uvula retractor arm has a plurality of clefts or holes defined therein for hooking the retractor onto a mouth gag once the uvula is properly retracted. A channel housing a fiber optic cable extends along the posterior side of the retractor. A fiber optic connector adapted for attachment to a light source extends from the retractor adjacent the handle. The inferior end of the retractor has at least one rib or support web beneath the raised platform, which supports the lower end of the channel and aims the light emitting end to illuminate the area behind the retracted uvula.

7 Claims, 5 Drawing Sheets

UVULA RETRACTOR AND UVULA RETRACTING SYSTEM

BACKGROUND

1. Field

The present disclosure relates to surgical instruments, and particularly to a uvula retractor having a fiber optic light and to a uvula retraction system including the retractor and a mouth gag modified for attachment of the uvula retractor in order to hold the uvula in a retracted state during a trans-oral nasopharyngeal procedure, such as an adenoidectomy, while illuminating a working area behind the uvula.

2. Description of the Related Art

The adenoid, also known as a pharyngeal tonsil, is a lymphatic tissue located in the nasopharynx. Adenoid hypertrophy (enlarged adenoids) is a common medical condition, especially in children. In such cases, an adenoidectomy is commonly performed. Therefore, this is one of the most common surgical procedures being performed, in some cases up to thousands of times a day.

An adenoidectomy is usually performed trans-orally. Since the adenoid is located in the nasopharynx, it is necessary to elevate the uvula and soft palate, often with a suction catheter, in order to visualize the adenoid. The uvula commonly becomes edematous and may suffer some form of ischemic damage, perhaps due to trauma caused by the catheter and/or other surgical instrument during the surgical procedure.

Additionally, since the adenoid is commonly accessed through the mouth, the working area is confined and poorly lit. Typically, an additional instrument is necessary for providing light to the working area, often by using light reflected from a mirror or a trans-nasal or trans-oral telescope, thus reducing the amount of space for the other surgical instruments to operate. Commonly used lighting instruments also require constant adjustment for proper lighting, which can be technically demanding.

Thus, a uvula retractor and uvula retracting system solving the aforementioned problems is desired.

SUMMARY

The uvula retractor is an elongate, arcuate body having a hooked handle at one end and a raised platform or flat spoon at the opposite end for lifting the uvula for access to the region behind the uvula. The uvula retractor arm has a plurality of clefts or holes defined therein for hooking the retractor onto a mouth gag once the uvula is properly retracted. A channel housing a fiber optic cable extends along the posterior side of the retractor. A fiber optic connector adapted for attachment to a light source extends from the retractor adjacent the handle. The inferior end of the retractor has at least one rib or support web beneath the raised platform, which supports the lower end of the channel and aims the light emitting end of the fiber optic cable at a 30-45° angle to illuminate the area behind the retracted uvula. The uvula retracting system includes a mouth gag and the attachable uvula retractor. The mouth gag is modified to include a post extending from an arm of the gag, which can be inserted into one of the clefts or holes in the retractor to maintain retraction of the uvula.

A method of uvula retraction includes retracting a uvula with the uvula retractor and retracting the uvula and soft palate away from the adenoid. The uvula retractor is then attached to the mouth gag by inserting the post into one of the cleft, which holds the uvula in a retracted position.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The uvula retractor provides a retractor with a built-in fiber optic cable to illuminate the area behind the uvula. The uvula retracting system includes the uvula retractor in combination with a mouth gag modified to support the retractor after proper retraction has been obtained. The uvula retractor is an elongate, arcuate body having a hooked handle at one end and a raised platform or flat spoon at the opposite end for lifting the uvula for access to the region behind the uvula. The uvula retractor arm has a plurality of clefts or holes defined therein for hooking the retractor onto a mouth gag once the uvula is properly retracted. A channel housing a fiber optic cable extends along the posterior side of the retractor. A fiber optic connector adapted for attachment extends from the retractor adjacent the handle. The inferior end of the retractor has at least one rib or support web beneath the raised platform, which supports the lower end of the channel and aims the light emitting end of the fiber optic cable at a 30-45° angle to illuminate the area behind the retracted uvula. The uvula retracting system includes a mouth gag and the attachable uvula retractor. The mouth gag is modified to include a post extending from an arm of the gag, which can be inserted into one of the clefts or holes in the retractor to maintain retraction of the uvula.

Figure 1:
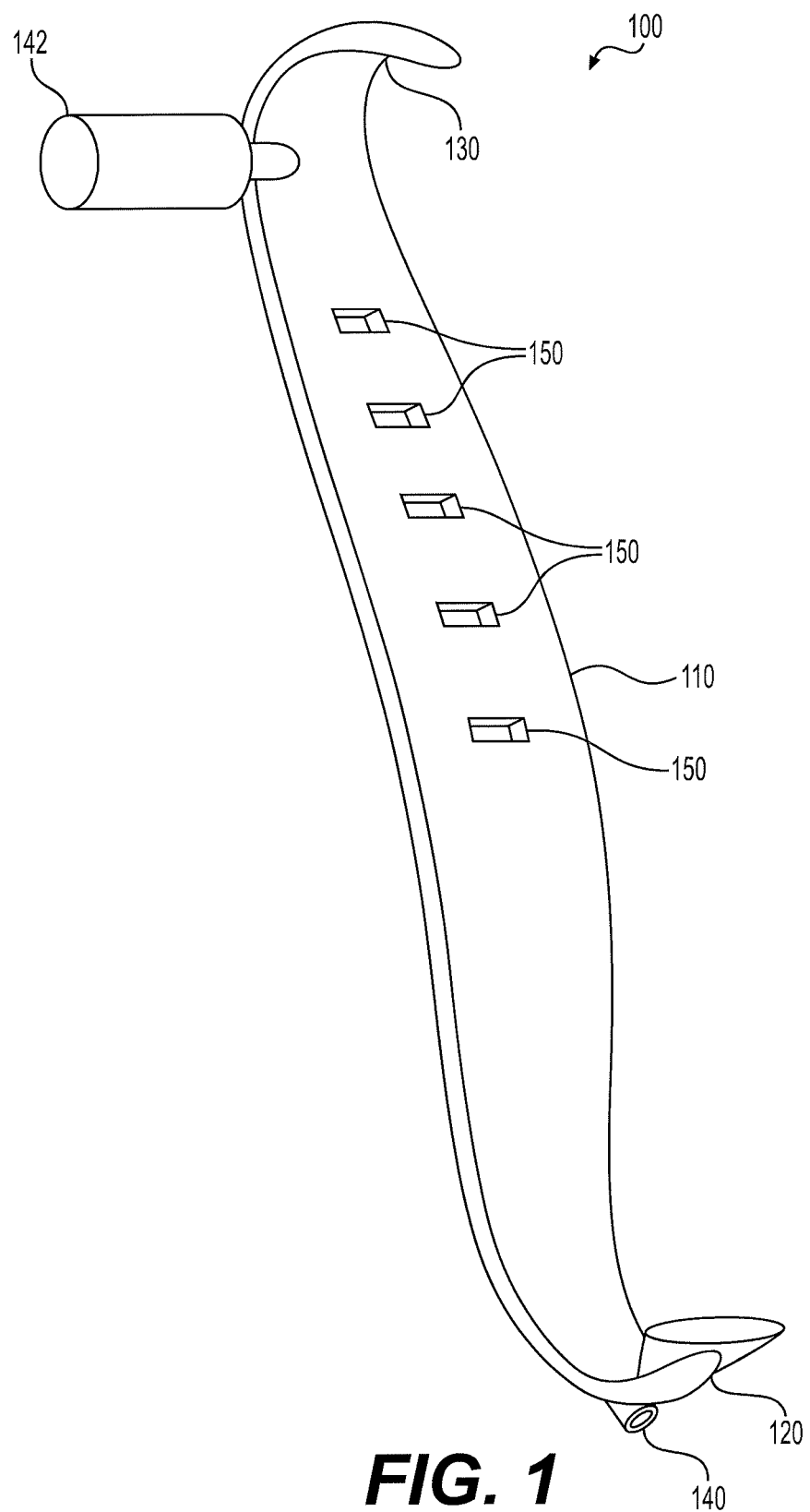
FIG. 1 is a perspective view of a uvula retractor.
Figure 5:
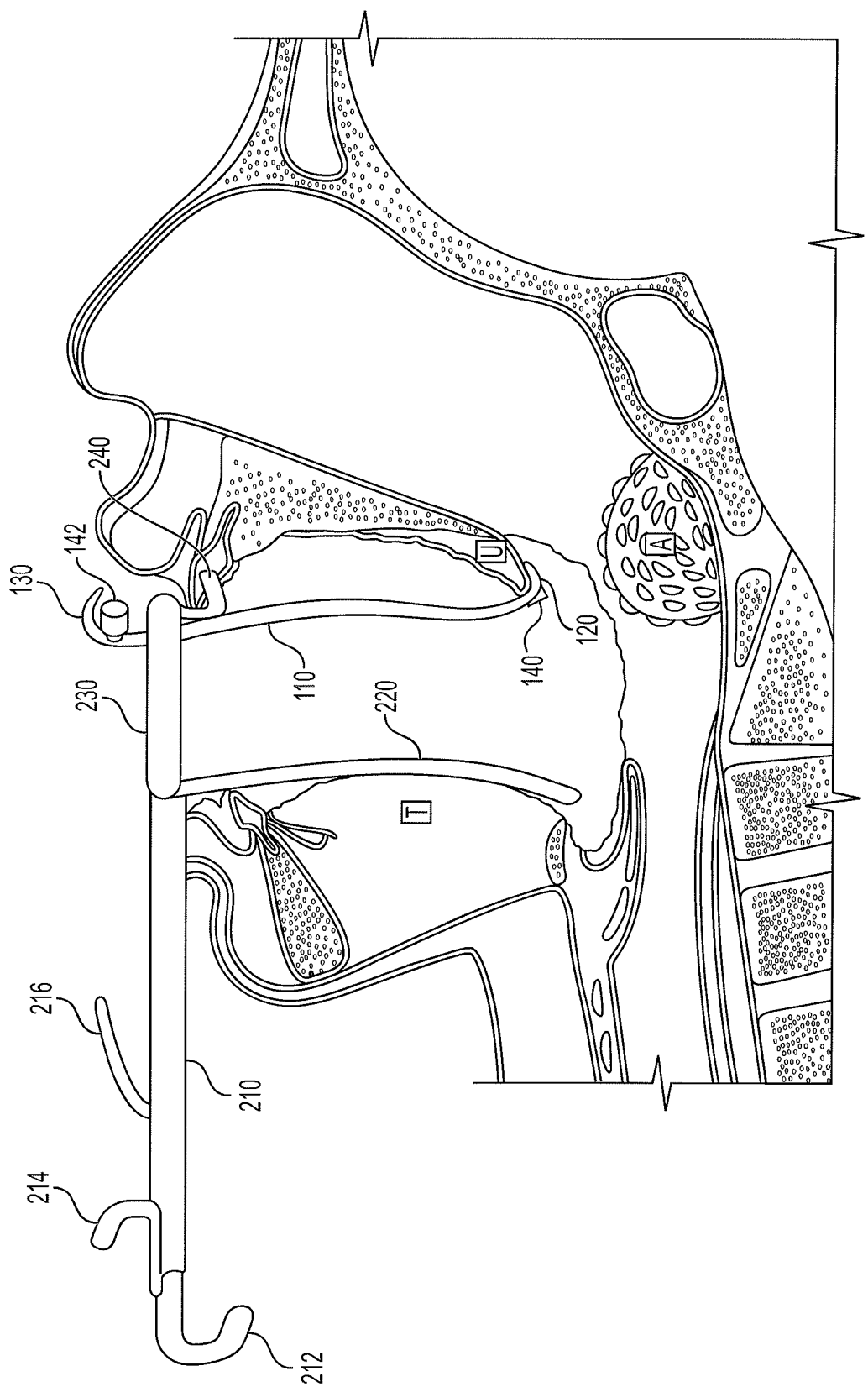
FIG. 5 is an environmental perspective view of the uvula retracting system of FIG. 4, shown retracting a uvula to provide access to the adenoid.

FIG. 1 shows an embodiment of the uvula retractor 100. The body 110 of the uvular retractor 100 defines an elongate strip having a raised platform 120 or flat spoon at its distal end for retracting the uvula and a hooked handle 130 at its proximal end. As shown in FIGS. 1 and 5, the handle 130 and the raised platform 120 both curve towards the anterior or front side of the body 110 of the retractor 100. A plurality of clefts 150 (or holes or slots) are spaced apart along the upper portion of the body 110 for facilitating connection to a mouth gag 200 (shown in FIGS. 2-3) by receiving a post 242 mounted on the mouth gag 200. The clefts 150 allow the position of the uvula retractor 100 to be adjusted in relation to the mouth gag 200 for accommodating patients having differently sized anatomical features.

The light emitting end 140 of a fiber optic cable extending through a channel on the posterior side of the body 110 of the retractor 100 may be supported on a rib or support web below the raised platform 120 and can be directed to illuminate the region behind the retracted uvula, which may include an adenoid and surrounding tissue. The light emitting end 140 of the fiber optic cable may be directed at an angle offset 30-45 degrees from a longitudinal axis of the body 110 towards the direction in which the raised platform 120 curves. The opposite end of the fiber optic cable includes a light source port 142 or connector adapted for connection to a light source extending from the retractor 100 adjacent the handle 130.

Figure 2:
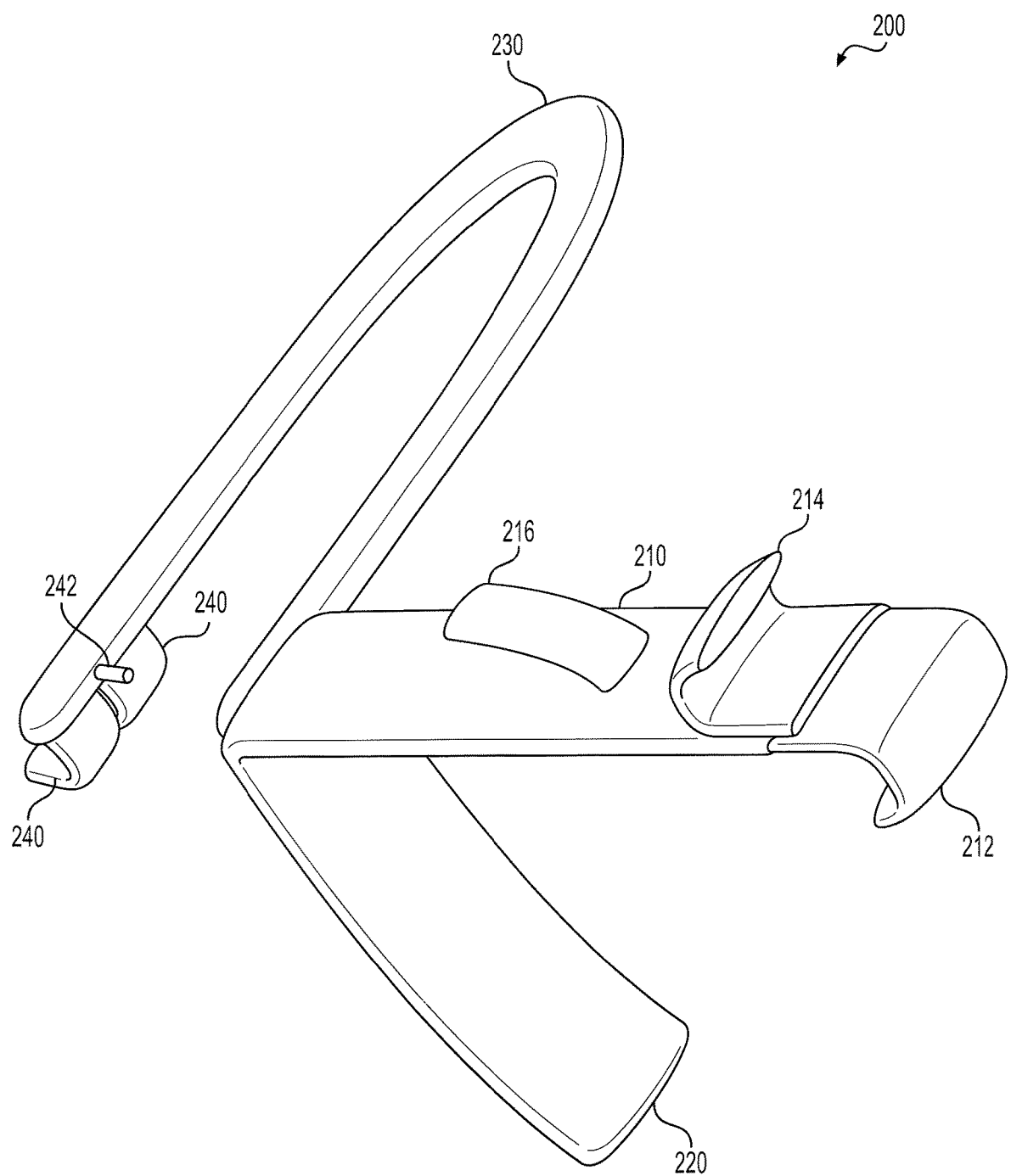
FIG. 2 is a perspective view of a mouth gag for use with the uvula retractor of FIG. 1.
Figure 3:
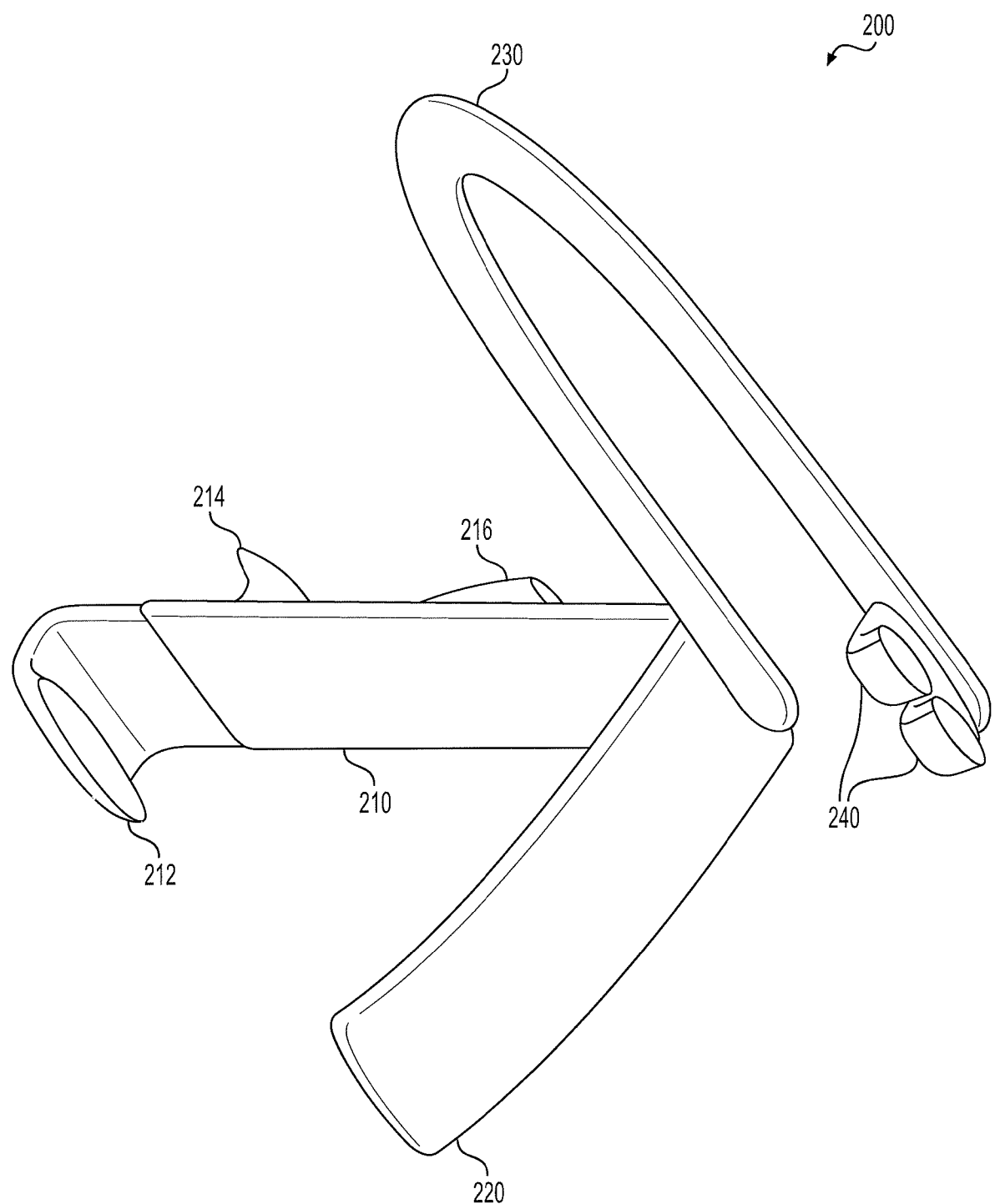
FIG. 3 is a perspective view of a mouth gag for use with the uvula retractor of FIG. 1, as seen from below.
Figure 4:
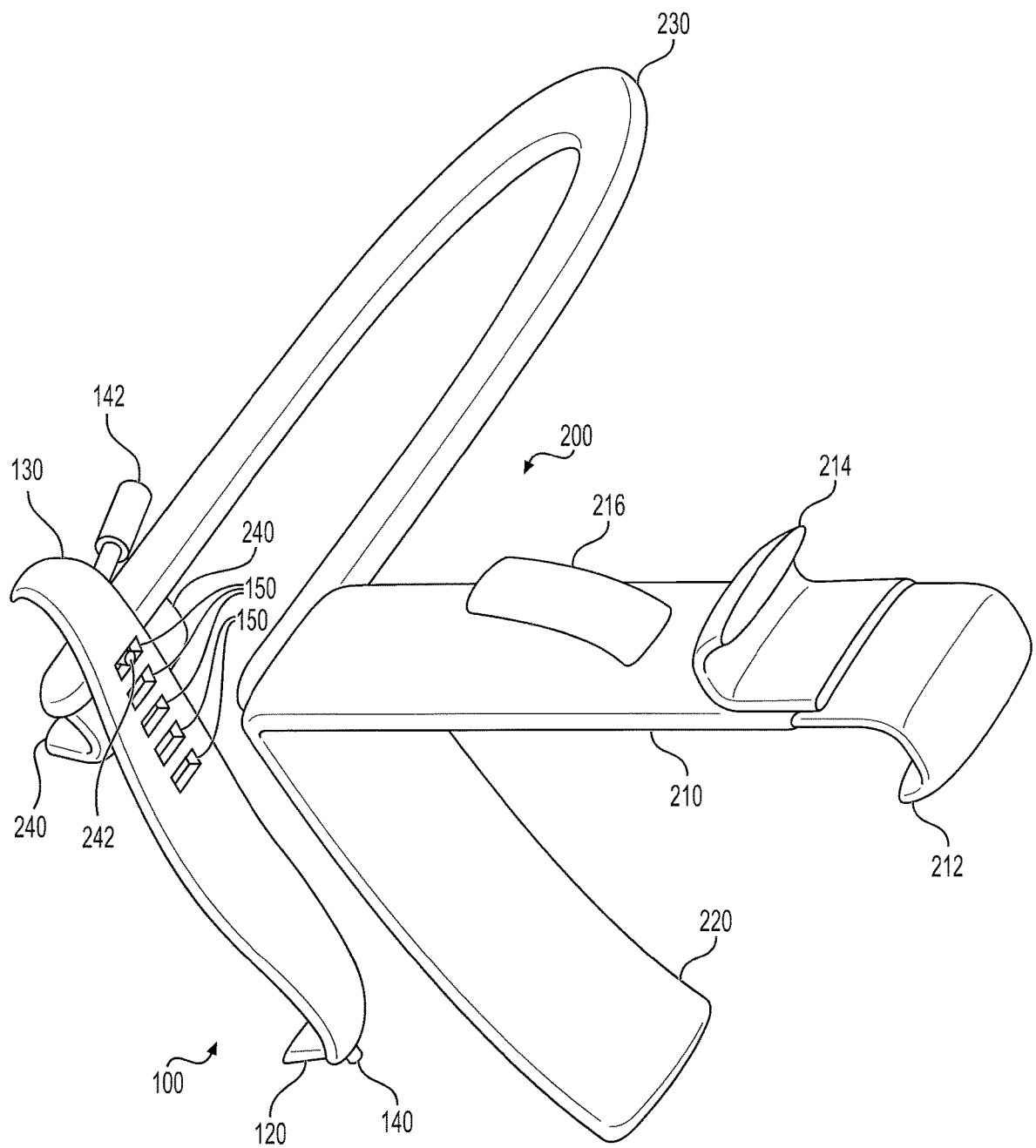
FIG. 4 is a perspective view of a uvula retracting system, showing the uvula retractor of FIG. 1 attached to the mouth gag of FIGS. 2 and 3.

FIGS. 2 and 3 depict an exemplary mouth gag 200 for use with the uvula retractor 100. The mouth gag 200 may include an elongate handle 210 having a downwardly extending first gripping hook 212 at its proximal end. An upwardly extending second gripping hook 214 may be positioned on the handle 210 distal from the first hook. An upwardly and distally extending projection 216 may extend out from the handle 210 distal to the second gripping handle 214.

A tongue depressor 220 may be attached to a distal end of the handle 210. The tongue depressor 220 may extend downward from the handle 210 and curve slightly back towards the handle 210 to follow a contour of a patient's tongue. A first terminal end of a U-shaped member 230 may be connected to the distal end of the handle 210 and an opposing second terminal end of the U-shaped member 230 may be connected to a downwardly extending jaw hook 240. The jaw hook 240 may include separated medial and lateral portions. The U-shaped member 230 may extend orthogonal to the tongue depressor 220 and the jaw hook 240. The opening in the U-shape may provide access to the patient's mouth and anatomical structures that are accessible through the mouth. A post 242 may extend out from a handle-facing side of the U-shaped member 230. The post 242 may be dimensioned and configured for insertion in the clefts 150 defined in the uvula retractor 100.

FIG. 5 shows the interaction of the uvula retractor 100 and the mouth gag 200 with anatomical features when installed in a position retracting the uvula (U). The mouth gag 200 is positioned to have the jaw hook 240 lodged under the patient's upper jaw and the tongue retractor 220 pushing the tongue (T) and chin downward to hold the mouth in an open position. The uvula retractor 100 is positioned at a top of the patient's mouth with the raised platform 120 holding the uvula (U) at a retracted position away from the adenoid (A). The uvula retractor 100 is connected to the mouth gag 200 through the post 242 on the mouth gag 200, which has been inserted into a cleft 150 on the uvula retractor 100. Accordingly, the uvula (U) and soft pallet are retracted to provide a view of the adenoid (A) and surrounding tissue, as well as a working space for a trans-oral operation, through the patient's mouth. The light emitting and 140 of the cable on the uvula retractor 100 is directed at the adenoid (A) and surrounding tissue, in a location that does not affect the surgical working area, thus obviating the need for an additional instrument to illuminate the working area.

A method of using the uvula retractor 100 and mouth gag 200 may include inserting the tongue depressor 220 of the mouth gag 200 over the patients tongue (T) and hooking the jaw hook 240 under the patient's upper jaw to retain the mouth in an open position. Once the mouth is retained open, the raised platform 120 of the uvula retractor 100 is inserted into the patient's mouth and used to retract the uvula (U) by pulling the uvula (U) away from the patient's adenoid (A). Once the uvula (U) is sufficiently retracted, the post 242 on the mouth gag 200 may be inserted into an appropriate cleft 150 on the uvula retractor 100, which maintains the position of the retractor 100 and retracted uvula (U).

It is to be understood that the uvula retractor and uvula retracting system is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A uvula retracting system, comprising:
   a uvula retractor, the uvula retractor including:
   an elongate, arcuate body having a proximal end, a distal end, an anterior side, a posterior side, and a length extending between the proximal and distal ends, the distal end of the body curving anteriorly and terminating in a raised platform, the raised platform being supported by a rib on the posterior side, and the proximal end of the body defining a handle having an anterior hook, the elongate body having a plurality of spaced clefts below the handle;
   a charnel extending between the proximal end of the body and the distal end of the body;
   a fiber optic cable extending through the channel, the cable having a light port extending from the body adjacent the handle, the light port being adapted for attachment to a light source, the cable having a light emitting end supported on the rib under the raised platform, the light emitting end being configured for supplying illumination behind the uvula after retraction of the uvula; and
   a mouth gag, the mouth gag including:
   an elongate handle having a proximal end and a distal end, the proximal end of the elongate handle defining a first gripping hook;
   a tongue depressor extending orthogonally from the distal end of the elongate handle;
   a U-shaped member having a first terminal end and an opposing second terminal end, the first terminal end being attached to the distal end of the elongate handle, the U-shaped member extending orthogonally from the distal end of the elongate handle, the U-shaped member extending orthogonally to the tongue depressor;
   a jaw hook extending from the second terminal end of the U-shaped member in a direction opposite the first terminal end; and
   a post extending out from the second terminal end of the U-shaped member in a direction towards the first terminal end;
   wherein the post is insertable into any one of the clefts of the uvula retractor to maintain the retractor in a position providing the desired retraction of a patient's uvula.

2. The uvula retracting system of claim 1, wherein the clefts of the uvula retractor are evenly spaced.

3. The uvula retracting system of claim 1, wherein the light emitting end of said cable is directed at an angle offset 30-45 degrees from the elongate body anteriorly.

4. The uvula retracting system of claim 1, wherein the raised platform defines a planar surface.

5. The uvula retracting system of claim 1, further comprising a second gripping hook connected to the elongate handle, wherein the second gripping hook is distal to the first gripping hook, the second gripping hook extending upwards and the first gripping hook extending downwards.

6. The uvula retracting system of claim 5, further comprising a distally extending projection connected to the handle distal to the second gripping hook.

7. The uvula retracting system of claim 1, wherein the jaw hook includes spaced medial and lateral portions.

\* \* \* \* \*